United States Patent
Ghosal

(10) Patent No.: US 6,224,906 B1
(45) Date of Patent: May 1, 2001

(54) ST. JOHN'S WORT COMPOSITION

(75) Inventor: Shibnath Ghosal, Varanasi (IN)

(73) Assignees: Natreon Inc., Highland Park, NJ (US); Indian Herbs Research & Supply Company Ltd. (IN)

(*) Notice: Subject to any disclaimer, the term of this patent is extended or adjusted under 35 U.S.C. 154(b) by 0 days.

(21) Appl. No.: 09/387,588

(22) Filed: Aug. 31, 1999

(51) Int. Cl.⁷ .............. A61K 9/20; A61K 9/14; A61K 9/48
(52) U.S. Cl. .......... 424/464; 424/195.1; 424/451; 424/455; 424/489; 514/937
(58) Field of Search ............... 424/489, 195.1, 424/451, 464, 455

(56) References Cited

U.S. PATENT DOCUMENTS 5,820,867 * 10/1998 Bewicke .............................. 424/195.1
6,113,907 *  9/2000 Khwaja et al. .................... 424/195.1

\* cited by examiner

*Primary Examiner*—James M. Spear
(74) *Attorney, Agent, or Firm*—Walter Katz

(57) ABSTRACT

A composition of St. John's Wort, in the form of a stable, free-flowing, powder, having effective antidepressant properties, characterized by having essentially no hypericin therein.

13 Claims, No Drawings

ST. JOHN'S WORT COMPOSITION

BACKGROUND OF THE INVENTION

1. Field of the Invention

This invention relates to St. John's wort compositions, and, more particularly, to such compositions in the form of a stable, free-flowing powder having effective antidepressant properties, characterized by having essentially no hypericin therein, and pharmaceutical and nutritional use formulations thereof.

2. Description of the Prior Art

St. John's wort is the common name for the plants *Hypericum perforatum* and *Hypericum augustifolia*; however, *Hypericum augustifolia* is rarely used in commercial products. Accordingly, the term as used herein refers to *Hypericum perforatum*, as its whole fresh or dried plant, and compositions and use formulations derived therefrom.

St. John's wort has been used externally to treat wounds, muscle aches and burns, and, internally, for relieving psychogenic disturbances, including depressive states, sleep disorders, anxiety and/or nervous excitement, particularly those associated with menopause. An advantage of treatment of certain cases of depression with St. John's wort is that it is rarely accompanied by sexual dysfunction, as with many prescription antidepressants. However, the art does not fully understand what chemical or chemicals in St. John's wort are responsible for its anti-depressant effect.

Accordingly, it is an object of this invention to provide a St. John's wort composition, and use formulations thereof, which have particularly effective antidepressant properties.

A feature of the invention is the provision of a stable, free-flowing St. John's wort powder composition which has essentially no hypericin therein.

Another feature of the invention is the provision of such composition with large amounts of phloroglucinols, xanthones and flavonoids therein.

These and other objects and features of the invention will be made apparent from the following description of the invention.

SUMMARY OF THE INVENTION

What is described herein is a composition of St. John's Wort, in the form of a stable, free-flowing, powder, having effective antidepressant properties, characterized by containing essentially no hypericin therein.

The composition includes a synergistic combination of at least 3% phloroglucinols and at least 3% xanthones therein and which also includes at least 7% flavonoids.

The composition comprises about 3–7% phloroglucinols including hyperforins, about 3–5% xanthones and about 7–12% flavonoids and is about 60% water soluble and about 70% ethanol soluble and has a total ash content of about 15%.

A pharmaceutical or nutritional formulation in the form of a tablet, capsule or liquid is provided for the composition herein. The formulation is present in suitable dosage form for oral administration.

A process of making the composition comprises (a) providing the freshly harvested upper one-third portion of the *Hypericum perforatum* plant at the time of flowering, (b) coarsely crushing the plant, (c) extracting exhaustively with 80% aqueous methanol or ethanol at 50° to 60° C., (d) concentrating the extract under vacuum below 60° C. to provide the dry solid, and (e) pulverizing the solid under controlled temperature and humidity conditions. Alternately, the coarsely crushed plant material is macerated before extraction with a solution of an antioxidant in order to improve the yield and stability of hyperforins.

DETAILED DESCRIPTION OF THE INVENTION

The St. John's wort powder composition of the invention is obtained by a process which comprises: (a) obtaining freshly harvested upper one-third portion of *Hypericum perforatum* plant at the time of flowering, (b) coarsely crushing the plant, (c) extracting exhaustively with 80% aqueous methanol or ethanol at 50° to 60° C., (d) concentrating the extract under vacuum below 60° C. to provide the dry solid, and (e) pulverizing the solid under controlled temperature and humidity.

The following are representative examples of the invention.

EXAMPLE 1

The concentration ranges of the bioactive constituents present in the extract of the *Hypericum perforatum* plant of Indian origin were determined in the following manner:

Test material:

*Hypericum perforatum* plants were collected from harvested and wild-crafted plants at the foot-hills and at altitudes of 1000–1200 m in the Northern Himalayas of India. Collections were made during the months of February to June, over a period of several years. The upper one-third portion of the fresh plants were extracted successively with n-heptane, chloroform and methanol. The respective extractives then were taken in suitable solvents and were subjected to comprehensive chromatographic and spectral analyses using markers.

Analytical techniques:

HPTLC and HPLC analyses were carried out routinely using different solvent systems to characterize and quantify the bioactive chemical constituents present in the extractives which gave an antidepressant effect.

Bioactive constituents:

The concentrations of the three major classes of bioactive constituents, namely, (i) Phloroglucinols; including hyperforins, (ii) Xanthones; and (iii) Flavonoids, including procyanidins, in these Indian *Hypericum perforatum* extracts, were found to vary greatly in both cultivated and wild-crafted samples due to several factors: (a) chemotype, (b) time of collection, (c) altitude of habitat, (d) fresh or delayed extraction, (e) use of natural antioxidants (e.g. vitamin-C or extract of *Emblica officinalis* plant) during extraction, and the conditions of preservation of the extractives. Optimum conditions were determined, and the varying ranges of concentrations of the ingredients are given in Table 1. The relative abundance of these bioactive constituents also is summarized in Table 1.

TABLE 1

Concentration Ranges of the Bioactive
Constituents of Indian Hypericum perforatum

| Compound type | Concentration (weight %) | Relative Abundance % Preserved |
|---|---|---|
| 1. Phloroglucinols including hyperforins | 3–7 | 15.1–25.1 |

TABLE 1-continued

Concentration Ranges of the Bioactive
Constituents of Indian Hypericum perforatum

| Compound type | Concentration (weight %) | Relative Abundance % Preserved |
|---|---|---|
| 2. Xanthones | 3–5 | 16.5–26.5 |
| 3. Flavonoids including procyanidins | 7-12 | 30.4–40.4 |
| 4. Hypericin | Trace | ~0 |
| 5. Other Active Compounds* | 5–9 | 18.9–28.9 |
| 6. Inactives | to 100% | Rest |

*These include carotenoids, tannoids, phenolic, fatty and amino acids and phytosteroids.

EXAMPLE 2

Example 1 was repeated except that the *Hypericum perforatum* plant material used was macerated with a solution of 0.5% antioxidant (for example, 0.5% aqueous solution of an extract of *Emblica officinalis*). HPLC analysis of the resulting extract showed a 15 to 32% increase in Hyperforin content when compared with the extract using no antioxidant.

EXAMPLE 3

The stability of Hyperforin in the presence and absence of Hypercin (singlet oxygen generator), and with an antioxidant fraction of *Emblica officinalis*, is summarized in Table 2 below.

TABLE 2

The Stability[1] of Hyperforin in Presence and Absence of (a) Hypericin and (b) Antioxidant

| Test Compound[2] | Relative Abundance of Hyperforin[3,4] | | |
|---|---|---|---|
| | Day-1 | Day-90 | Day-180 |
| 1. Hyperforin[6] | 30.0 ± 6.6 | 24.3 ± 3.5 | 16.4 ± 2.9 |
| 2. Hyperforin in presence of Hypericin[5] added to the extract | 25.4 ± 5.3 | 18.5 ± 3.9 | 7.4 ± 1.4 |
| 3. Hyperforin + Antioxidant[7] | 28.8 ± 4.5 | 27.7 ± 3.9 | 22.1 ± 2.0 |
| 4. Hyperforin + Antioxidant[7] + Hypericin[5] | 32.7 ± 4.4 | 25.9 ± 3.8 | 18.3 ± 3.3 |

[1]Mean of three replicates in each case.
[2]Hypericum extract: upper one-third portion of plant, collected at flowering time, extracted with aqueous methanol (20:80); yield of total phenolics 15 ± 2% of dry wt. of plant material.
[3]The remaining constituents (%) comprise phenolics (e.g; xanthonoids, flavonoids) other than hyperforin.
[4]Determined by HPTLC using markers (solvent systems: toluene-ethyl acetate, 93:07; ethyl acetate-formic acid-acetic acid-water, 100:11:11:27; detection, quenching mode; wavelength, 260 nm.
[5]Ratio of Hyperforin: Hypericin affer admixture (100:10).
[6]Hyperforin in absence of Hypericin.
[7]Hyperforin (with or without Hypericin) + Antioxidant (100:0.5, w/w).

These results demonstrate also that added antioxidant enhances the stability of Hyperforin both in the absence and presence of Hypericin (a generator of a singlet oxygen). The per se, time-dependent degradation of Hyperforin is also thwarted by the antioxidant. The antioxidant used was the antioxidant fraction of the *Emblica Officinalis* plant.

The presence of a large amount of xanthones (>3%) in the composition of the invention also results in increased storage; stability, otherwise, on storage, the hypeforin active constituent degrades into inactive compounds.

EXAMPLE 4

Determination of Antidepression Effect of Hyperforins (Hfs.) and Xanthones (Xns.) of Hypericum Extract Composition in Albino Rats Animals.

CF rats (200–220 g b.w.)

Test model.

Porsolt's behavioral despair model (Willner P. (1984). The validity of animal model of depression, *Psychopharmacol.* 83, 1–16).

Test compounds.

Hyperforins (Hfs., hyperforin and derivatives, rel. abundance ca. 78%; adhyperforin, 8%; prenylated phloroglucinols, ca. 12%, as determined by HPTLC using markers and LC-MS), isolated from the Indian Hypericum extract (cultivated plant, harvested at flowering time) and compared with the Hfs. Present in Movana tablet.

Polyoxygenated xanthones.

[Xns., 1,3,5-trioxygenated (viz. 1-hydroxy-3,5-dimethoxyxanthone, relative abundance 43%; 1,3-dihydroxy-5-methoxyxanthone, 5%); 1,3,5,6-tetraoxygenated (viz. 1-hydroxy-3,5,6-trimethoxyxanthone, rel. abundance, 14%); 1,3,6,7-tetraoxygenated (1-hydroxy-3,6,7-trimethoxyxanthone, 10%); and 2-C-glucosyl-1,3,6,7-tetraoxygenated xanthone (rel. abundance, 24%)], isolated from the Indian Hypericum extract and identified by direct comparison (HPTLC, HPLC, GC-MS of O-TMS derivatives) with synthetic markers (Ghosal et al. (1975) *J. Pharm. Sci.* 64, 80–83; (1974) *JCS Perkin I*, 2538–2542; (1978) *Phytochemistry*, 17, 2119–2123).

Treatment.

The test compounds (suspended in 0.3 CMC in distilled water) were administered orally (p.o.) for 5 consecutive days. The results are incorporated in Table 1.

TABLE 3

Antidepressant Effect of Hyperforins[1] and Xanthones[1] from Indian Hypericum Perforatum Extract, Alone and in Combination, in Albino Mice[2]

| Treatment | Dose Mg/kg b.w. | Immobility Period (Seconds)* (Porsolt's method) |
|---|---|---|
| Vehicle treated | | |
| Control | — | 152 ± 5.80 |
| Hyperforins | 1.0 | 108.53 ± 6.12 |
| | 2.5 | 96.42 ± 5.53 |
| | 5.0 | 80.83 ± 3.02* |
| Xanthones | 1.0 | 98.10 ± 8.17 |
| | 2.5 | 80.09 ± 4.55* |
| | 5.0 | 55.06 ± 3.49** |
| Hyperforins + Xanthones | 0.5 + 0.5 | 68.62 ± 4.77* |
| | 1.25 + 1.25 | 52.11 ± 2.08** |
| | 2.5 + 2.5 | 58.88 ± 3.17** |
| Hyperforins + Xanthones + Hypericin[3] | 0.5 + 0.5 + 0.1 | 95.19 ± 7.55 |
| | 1.0 + 1.0 + 0.5 | 112.11 ± 6.88 |
| | 1.0 + 1.0 + 1.0 | 134.42 ± 5.54 | n = 10 to 12; values are expressed as Mean ± SEM; significance

TABLE 3-continued

Antidepressant Effect of Hyperforins[1] and Xanthones[1] from
Indian Hypericum Perforatum Extract,
Alone and in Combination, in Albino Mice[2]

| Treatment | Dose Mg/kg b.w. | Immobility Period (Seconds)* (Porsolt's method) |
|---|---|---|

(P * <0.01, ** <0.001) in relation to vehicle-treated control group
(statistical significance calculated by ANOVA followed by Newmann-Keul's test);
[1]See Scheme-1;
[2]Albino rats also exhibited antidepressant effect to similar extent;
[3]Hypericin per se did not exhibit any antidepressant effect at the dose levels tested.
*The higher values indicate a reduced antidepressant effect Accordingly, xanthones produce a cascade of events, including inhibition of re-uptake of neurotransmitters at presynaptic level. This causes augmentation of neurotransmitters at presynaptic level and result in pronounced antidepressant effect especially in combination with hyperforins. However, the molecular mechanism of the synergistic effect of the hyperforins-xanthonoids combination is, at present, not clearly understood.

EXAMPLE 6

The antidepressant effect of the three extracts (5a, 5b and 5c) was tested in several animal models for psychotropic activity according to the method described by S. N. Okpanyi and M. L. Weischer, in *Arzneim. Forsc.*, 1987, 37, 10–13. Extract 5a with essentially no hypericin, was found to be substantially more effective than the commercial extracts 5b and 5c, containing 0.3% hypericin.

EXAMPLE 7

Tablets and Capsules

| Ingredient | Composition (w/w, in %) | Quantity per tablet (mg) |
|---|---|---|
| 1. St. John's Wort extract of Ex. 1 | 60.0 | 250.0 |
| 2. Avicel pH 101 | 20.0 | 84.0 |
| 3. Starch 1500 | 17.5 | 75.5 |
| 4. Stearic acid, N.F. (powder) | 2.0 | 8.5 |
| 5. Cab-O-Sil | 0.5 | 2.0 |

Note: St. John's Wort extract of invention is granulated with starch paste to make it a free-flowing powder. Blend all the ingredients, except 4, for 25 min. in a blender. Screen in 4 and blend for an additional 5 min. Compress into tablets using 7/16-in standard concave tooling. Alternately, the blended material can be filled into appropriate capsules.

EXAMPLE 8

Chewable Tablets

| Ingredient | Composition (w/w, in %) | Quantity per tablet (mg) |
|---|---|---|
| 1. St. Johns Wort extract of Ex.1 | 12.26 | 27.60 |
| 2. Sodium ascorbate, USP | 36.26 | 81.60 |
| 3. Avicel pH 101 | 17.12 | 38.50 |
| 4. Sodium saccharin, (powder), N.F. | 0.56 | 1.25 |
| 5. DiPac | 29.30 | 66.00 |
| 6. Stearic acid, N.F. | 2.50 | 5.60 |
| 7. Imitation orange Flavor | 1.0 | 2.25 |
| 8. FD & C Yellow #6 dye | 0.5 | 1.12 |
| 9. Cab-O-Sil | 0.5 | 1.12 |

Blend all the ingredients, except 6, for 20 min in a blender. Screen in 6 and blend for an additional 5 min. Compress into tablets using 7/16-in standard concave tooling.

EXAMPLE 9

"Maintenance" Multivitamin Tablets or Capsules

| Ingredient | Composition (w/w. in %) | Quantity per tablet (mg) |
|---|---|---|
| 1. Vitamin A acetate (dry form 500 IU and 500 $D_2$ per mg) | 5.5 | 11.0 |
| 2. Thiamine mono-nitrate, USP | 0.8 | 1.65 |
| 3. Riboflavin, USP | 1.1 | 2.10 |
| 4. Pyridoxine HCl, USP | 1.0 | 2.10 |
| 5. 1% Cyanocobalamine (in gelatin) | | |
| 6. D-Calcium pantothenate, USP | 3.75 | 7.50 |
| 7. St. John's Wort extract of Ex. 1, free-flowing | 33.25 | 66.50 |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid, (powder), N.F. | 1.5 | 3.00 |
| 13. Magnesium stearate, (powder), N.F. | 1.0 | 2.00 |

Blend all ingredients for 20 min in a suitable blender. Screen in 12 and blend for an additional 5 min. Compress at a tablet weight of 200 mg using 3/8-in standard concave tooling. Alternately, blended material is filled into a capsule containing 200 mg of multi-vitamins. These tablets or capsules can be used as nutritional supplements.

EXAMPLE 10

Geriatric Formula Vitamin Tablets

| Ingredient | Composition (w/w. in %) | Quantity per tablet (mg) |
|---|---|---|
| 1. Ferrous sulfate, USP 95% Ethecal granulation | 15.00 | 78.00 |
| 2. Thiamine mono-nitrate, USP | 1.09 | 6.00 |
| 3. Riboflavin, USP | 1.00 | 5.50 |
| 4. Niacinamide, USP | 6.00 | 33.00 |

-continued

Geriatric Formula Vitamin Tablets

| Ingredient | Composition (w/w. in %) | Quantity per tablet (mg) |
| --- | --- | --- |
| 5. St. John's Wort extract of Ex. 1 free-flowing powder | 17.45 | 96.00 |
| 6. Ascorbic acid USP fine crystal | 15.00 | 78.00 |
| 7. Calcium pantothenate, USP | 0.73 | 4.00 |
| 8. Pyridoxine HCl, USP | 0.14 | 0.75 |
| 9. Cyanocobalmine, 0.1% spray dried | 0.82 | 4.50 |
| 10. AcDisol | 2.00 | 11.00 |
| 11. Stearic acid, (powder), N.F. | 2.00 | 11.00 |
| 12. Magnesium stearate, (powder), N.F. | 0.25 | 1.38 |
| 13. CeloCat | 38.52 | 211.87 |

Prepare a premix of items 2, 3, 6, 7. Mix in other ingredients except 10 and 11 and blend for an additional 5 min. Compress using oval punches (1=0.480 in., w=0.220× cup=0.040 in.) Sugar or film coat. These tablets can be used as nutritional supplements.

EXAMPLE 11

Elixir Formula

| Ingredient | Quantity |
| --- | --- |
| 1. St. John's Wort extract of Ex. 1 | 0.2 g |
| 2. Lemon Tincture | 5.0 ml |
| 3. Orange Tincture | 5.0 ml |
| 4. Sodium Saccharin | 0.5 g |
| 5. Propylene Glycol | 65.0 ml |
| 6. Glycerine | 15.0 ml |
| 7. Sorbitol, USP, sufficient quantity to make | 100.0 ml |

Dissolve 1 in 5 and 6 which have been heated to 50° C. Dissolve 4 in 2 and 3 and add the solution of St. John's Wort extract at 25° C. Add sufficient sorbitol to make the product measure 100 ml.

In summary, the present invention provides a composition of St. John's Wort, in the form of a stable, free-flowing powder, characterized by containing essentially no hypericin therein, and pharmaceutical and nutritional use formulations thereof, which are effective antidepressant products. In the preferred form of the invention, the composition includes at least 3% by weight phloroglucinols, and at least 3% xanthones, most preferably with at least 7% flavonoids. The synergistic combination of these active constituents provides long-term storage stability for the composition and formulations, and a significantly enhanced antidepressive effect for the user, as compared to commercial St. John's Wort products.

The extract composition of the invention, with essentially no hypericin therein, can be used which is such, if desired, without dilution, as required by present St. John's Wort products to reduce its hypericin content to reasonable levels albeit with a substantial reduction in the relative abundance of phloroglucinols, xanthones and flavonoid actives therein.

While the invention has been described with particular reference to certain embodiments thereof, it will be understood that changes and modifications may be made which are within the skill of the art. Accordingly, it is intended to be bound only by the following claims, in which:

What is claimed is:

1. A composition of St. John's Wort, in the form of a stable, free-flowing powder, having effective antidepressant properties, characterized by having essentially no hypericin therein, and, by weight, a synergistic combination of at least 3% phloroglucinols including hyperforins, and at least 3% xanthones.

2. A composition according to claim 1 which also includes an antioxidant.

3. A process of making the composition of claim 1 which comprises (a) providing the freshly harvested upper one-third portion of the *Hypericum perforatum* plant at the time of flowering, (b) coarsely crushing the plant, (c) extracting exhaustively with 80% aqueous methanol or ethanol at 50° to 60° C., (d) concentrating the extract under vacuum below 60° C. to provide the dry solid, and (e) pulverizing the solid under controlled temperature and humidity conditions.

4. A composition according to claim 1 which also includes at least 7% flavonoids.

5. A composition according to claim 1 comprising about 3–7% phloroglucinols including hyperforins, about 3–5% xanthones and about 7–12% flavonoids.

6. A composition according to claim 5 which is about 60% water soluble and about 70% ethanol soluble.

7. A composition according to claim 5 which has a total ash content of about 15%.

8. A pharmaceutical or nutritional formulation in the form of a tablet, capsule or liquid which includes the composition of claim 1.

9. A pharmaceutical or nutritional formulation in the form of a tablet, capsule or liquid which includes the composition of claim 5.

10. A pharmaceutical or nutritional formulation in the form of a tablet, capsule or liquid which includes the composition of claim 4.

11. A formulation according to claim 8 which is present in suitable dosage form for oral administration.

12. A process of claim 3 where the coarsely crushed plant material is macerated with a solution of an antioxidant.

13. A method of treating depression which comprises administering a formulation of claim 8.

\* \* \* \* \*